United States Patent
Babkin

(10) Patent No.: US 10,543,032 B2
(45) Date of Patent: Jan. 28, 2020

(54) PRESSURE MODULATED CRYOABLATION SYSTEM AND RELATED METHODS

(71) Applicant: ADAGIO MEDICAL, Inc., Laguna Hills, CA (US)

(72) Inventor: Alexei Babkin, Dana Point, CA (US)

(73) Assignee: Adagio Medical, Inc., Laguna Hills, CA (US)

(*) Notice: Subject to any disclaimer, the term of this patent is extended or adjusted under 35 U.S.C. 154(b) by 990 days.

(21) Appl. No.: 14/919,681

(22) Filed: Oct. 21, 2015

(65) Prior Publication Data

US 2016/0135864 A1   May 19, 2016

Related U.S. Application Data

(60) Provisional application No. 62/079,299, filed on Nov. 13, 2014.

(51) Int. Cl.
*A61B 18/02* (2006.01)
*A61B 18/00* (2006.01)

(52) U.S. Cl.
CPC .... *A61B 18/02* (2013.01); *A61B 2018/00041* (2013.01); *A61B 2018/00404* (2013.01); *A61B 2018/00577* (2013.01); *A61B 2018/0212* (2013.01)

(58) Field of Classification Search
CPC .................................................... A61B 18/02
See application file for complete search history.

(56) References Cited

U.S. PATENT DOCUMENTS

| | | |
|---|---|---|
| 3,062,017 A | 11/1962 | Balcar |
| 3,613,689 A | 10/1971 | Crump |
| 3,889,680 A | 6/1975 | Armao |
| 3,942,010 A | 3/1976 | Peterson |
| 3,993,123 A | 11/1976 | Chu |
| 4,034,251 A | 7/1977 | Haas |
| 4,167,771 A | 9/1979 | Simons |
| 4,226,281 A | 10/1980 | Chu |
| 4,281,268 A | 7/1981 | Sawa |

(Continued)

FOREIGN PATENT DOCUMENTS

| | | |
|---|---|---|
| GB | 1422535 | 1/1976 |
| GB | 2283678 | 6/1996 |

(Continued)

OTHER PUBLICATIONS

International Search Report for PCT/US2015/056780, dated Jan. 5, 2016.

(Continued)

*Primary Examiner* — Michael F Peffley
*Assistant Examiner* — Bo Ouyang
(74) *Attorney, Agent, or Firm* — Richard Batt

(57) ABSTRACT

A near critical fluid based cryoablation system comprises a cryoablation catheter for creating a lesion in tissue. A cryogenic fluid is transported under pressure through the catheter. A controller adjusts the pressure from a relatively high (e.g., near critical) pressure to a substantially lower pressure based on a condition during the catheter activation. In one configuration, the pressure is modulated based on the temperature of the catheter. When the temperature of the catheter reaches a target temperature, the pressure is reduced.

18 Claims, 11 Drawing Sheets

(56) References Cited

U.S. PATENT DOCUMENTS

| | | |
|---|---|---|
| 4,384,360 A | 5/1983 | Kitadate |
| 4,418,421 A | 11/1983 | Kitadate |
| 4,519,389 A | 5/1985 | Gudkin |
| 4,548,045 A | 10/1985 | Aitares |
| 4,802,475 A | 2/1989 | Weshahy |
| 4,838,041 A | 6/1989 | Bellows |
| 4,843,446 A | 6/1989 | Nishino |
| 4,945,562 A | 7/1990 | Staub |
| 4,946,460 A | 8/1990 | Merry |
| 4,982,080 A | 1/1991 | Wilson |
| 5,012,505 A | 4/1991 | Zupancic |
| 5,037,395 A | 8/1991 | Spencer |
| 5,108,390 A | 4/1992 | Potocky |
| 5,147,355 A | 9/1992 | Friedman |
| 5,147,538 A | 9/1992 | Wright |
| 5,155,093 A | 10/1992 | Den |
| 5,173,606 A | 12/1992 | Weinberger |
| 5,211,646 A | 5/1993 | Alperovich |
| 5,212,626 A | 5/1993 | Bella |
| 5,214,925 A | 6/1993 | Hoy |
| 5,237,824 A | 8/1993 | Pawliszyn |
| 5,254,116 A | 10/1993 | Baust |
| 5,274,237 A | 12/1993 | Gallagher |
| RE34,502 E | 1/1994 | Webster |
| 5,275,595 A | 1/1994 | Dobak, III |
| 5,324,286 A | 6/1994 | Fowler |
| 5,334,181 A | 8/1994 | Rubinsky |
| 5,369,384 A | 11/1994 | Woods |
| 5,400,602 A | 3/1995 | Chang |
| 5,405,533 A | 4/1995 | Hazleback |
| 5,417,072 A | 5/1995 | Silver |
| 5,433,717 A | 7/1995 | Rubinsky |
| 5,452,582 A | 9/1995 | Longsworth |
| 5,471,844 A | 12/1995 | Levi |
| 5,494,039 A | 2/1996 | Onki |
| 5,504,924 A | 4/1996 | Ohashi |
| 5,520,682 A | 5/1996 | Baust |
| 5,531,742 A | 7/1996 | Barken |
| 5,573,532 A | 11/1996 | Chang |
| 5,603,221 A | 2/1997 | Maytal |
| 5,661,980 A | 9/1997 | Gallivan |
| 5,702,435 A | 12/1997 | Maytal |
| 5,716,353 A | 2/1998 | Matsura |
| 5,733,280 A | 3/1998 | Avitall |
| 5,741,248 A | 4/1998 | Stern |
| 5,757,885 A | 5/1998 | Yao |
| 5,800,487 A | 9/1998 | Mikus |
| 5,800,488 A | 9/1998 | Crockett |
| 5,816,052 A | 10/1998 | Foote |
| 5,885,276 A | 3/1999 | Ammar |
| 5,899,897 A | 5/1999 | Rabin |
| 5,899,898 A | 5/1999 | Arless |
| 5,899,899 A | 5/1999 | Arless |
| 5,901,783 A | 5/1999 | Dobak, III |
| 5,910,104 A | 6/1999 | Dobak, III |
| 5,916,212 A | 6/1999 | Baust |
| 5,924,975 A | 7/1999 | Goldowsky |
| 5,947,960 A | 9/1999 | Griswold |
| 5,950,444 A | 9/1999 | Matsunagar |
| 5,957,963 A | 9/1999 | Dobak |
| 5,978,697 A | 11/1999 | Maytal |
| 5,993,444 A | 11/1999 | Ammar |
| 5,997,781 A | 12/1999 | Nishikawa |
| 6,004,269 A | 12/1999 | Crowley |
| 6,039,730 A | 3/2000 | Rabin |
| 6,074,412 A | 6/2000 | Mikus |
| 6,096,068 A | 8/2000 | Dobak |
| 6,106,518 A | 8/2000 | Wittenberger |
| 6,139,544 A | 10/2000 | Mikus |
| 6,142,991 A | 11/2000 | Schatzberger |
| 6,161,543 A | 12/2000 | Cox |
| 6,171,277 B1 | 1/2001 | Ponzi |
| 6,179,831 B1 | 1/2001 | Bilweis |
| 6,182,666 B1 | 2/2001 | Dobak, III |
| 6,190,378 B1 | 2/2001 | Jarvinen |
| 6,190,382 B1 | 2/2001 | Ormsby |
| 6,193,644 B1 | 2/2001 | Dobak, III |
| 6,198,974 B1 | 3/2001 | Webster |
| 6,235,018 B1 | 5/2001 | Lepivert |
| 6,237,355 B1 | 5/2001 | Li |
| 6,241,722 B1 | 6/2001 | Dobak |
| 6,251,105 B1 | 6/2001 | Mikus |
| 6,263,046 B1 | 7/2001 | Rogers |
| 6,270,493 B1 | 8/2001 | Lalonde |
| 6,307,916 B1 | 10/2001 | Rogers |
| 6,324,852 B1 | 12/2001 | Cheng |
| 6,341,629 B1 | 1/2002 | Clark |
| 6,347,675 B1 | 2/2002 | Kolle |
| 6,355,029 B1 | 3/2002 | Joye |
| 6,368,304 B1 | 4/2002 | Aliberto |
| 6,377,659 B1 | 4/2002 | Snyder |
| 6,396,901 B1 | 5/2002 | Heil |
| 6,432,174 B1 | 8/2002 | Heung |
| 6,440,126 B1 | 8/2002 | Abboud |
| 6,451,011 B2 | 9/2002 | Tu |
| 6,471,694 B1 | 10/2002 | Kudaravalli |
| 6,475,212 B2 | 11/2002 | Dobak |
| 6,477,231 B2 | 11/2002 | Snyder |
| 6,486,078 B1 | 11/2002 | Rangarajan |
| 6,520,933 B1 | 2/2003 | Evans |
| 6,527,765 B2 | 3/2003 | Kelman |
| 6,530,420 B1 | 3/2003 | Takada |
| 6,537,271 B1 | 3/2003 | Murray |
| 6,544,176 B2 | 4/2003 | Mikus |
| 6,551,309 B1 | 4/2003 | LePivert |
| 6,554,797 B1 | 4/2003 | Worthen |
| 6,572,610 B2 | 6/2003 | Kovalcheck |
| 6,584,332 B2 | 6/2003 | Yoshitake |
| 6,602,276 B2 | 8/2003 | Dobak, III |
| 6,622,494 B1 | 9/2003 | Pourrahimi |
| 6,622,507 B2 | 9/2003 | Cotte |
| 6,628,002 B2 | 9/2003 | Ritz |
| 6,648,879 B2 | 11/2003 | Joye |
| 6,685,720 B1 | 2/2004 | Wu |
| 6,706,037 B2 | 3/2004 | Zvuloni |
| 6,726,653 B2 | 4/2004 | Noda |
| 6,737,225 B2 | 5/2004 | Miller |
| 6,746,445 B2 | 6/2004 | Abboud |
| 6,767,346 B2 | 7/2004 | Damasco |
| 6,812,464 B1 | 11/2004 | Sobolewski |
| 6,848,502 B2 | 1/2005 | Bishop |
| 6,848,458 B1 | 2/2005 | Shrinivasan |
| 6,893,419 B2 | 5/2005 | Noda |
| 6,893,433 B2 | 5/2005 | Lentz |
| 6,905,492 B2 | 6/2005 | Zvuloni |
| 6,936,045 B2 | 8/2005 | Yu |
| 6,941,953 B2 | 9/2005 | Feld |
| 6,989,009 B2 | 1/2006 | Lafontaine |
| 7,004,937 B2 | 2/2006 | Lentz |
| 7,022,120 B2 | 4/2006 | Lafontaine |
| 7,083,612 B2 | 8/2006 | Littrup |
| 7,110,506 B2 | 9/2006 | Radley |
| 7,160,290 B2 | 1/2007 | Eberl |
| 7,220,252 B2 | 5/2007 | Shah |
| 7,220,257 B1 | 5/2007 | Lafontaine |
| 7,195,625 B2 | 7/2007 | Lentz |
| 7,258,161 B2 | 8/2007 | Cosley |
| 7,273,479 B2 * | 9/2007 | Littrup ............... A61B 18/02 128/898 |
| 7,410,484 B2 | 8/2008 | Littrup |
| 7,648,497 B2 | 1/2010 | Lane |
| 7,740,627 B2 | 6/2010 | Gammie |
| 7,842,031 B2 | 11/2010 | Abboud |
| 8,012,147 B2 | 9/2011 | Lafontaine |
| 8,080,005 B1 | 12/2011 | Berzak et al. |
| 8,177,780 B2 | 5/2012 | Cox |
| 8,298,217 B2 | 10/2012 | Lane |
| 8,387,402 B2 | 3/2013 | Littrup |
| 8,475,441 B2 | 7/2013 | Babkin |
| 8,641,704 B2 | 2/2014 | Werneth |
| 8,685,014 B2 | 4/2014 | Babkin |
| 8,740,891 B2 | 6/2014 | Babkin |
| 8,740,892 B2 | 6/2014 | Babkin |
| 8,845,628 B2 | 9/2014 | Babkin |

(56) References Cited

U.S. PATENT DOCUMENTS

| | | |
|---|---|---|
| 8,888,768 B2 | 11/2014 | Babkin |
| 8,945,106 B2 | 2/2015 | Arless |
| 9,095,320 B2 | 8/2015 | Littrup |
| 2001/0024485 A1 | 9/2001 | Rogers |
| 2001/0047134 A1 | 11/2001 | Holdaway |
| 2002/0049409 A1 | 4/2002 | Noda |
| 2002/0062831 A1 | 5/2002 | Beyar |
| 2002/0072741 A1 | 6/2002 | Silwa |
| 2002/0087152 A1 | 7/2002 | Mikus |
| 2002/0151331 A1 | 10/2002 | Abdelmonem |
| 2003/0040740 A1 | 2/2003 | Kovalcheck |
| 2003/0055415 A1 | 3/2003 | Yu |
| 2003/0195605 A1 | 10/2003 | Kovalcheck |
| 2003/0199817 A1 | 10/2003 | Thompson |
| 2004/0027462 A1 | 2/2004 | Hing |
| 2004/0118144 A1 | 6/2004 | Hsu |
| 2004/0148004 A1 | 7/2004 | Wallsten |
| 2004/0215295 A1 | 10/2004 | Littrup |
| 2005/0027289 A1 | 2/2005 | Castellano |
| 2005/0198972 A1 | 9/2005 | Lentz et al. |
| 2005/0209587 A1 | 9/2005 | Joye |
| 2005/0261573 A1 | 11/2005 | Littrup |
| 2006/0235375 A1 | 6/2006 | Littrup |
| 2006/0212028 A1 | 9/2006 | Joye |
| 2006/0235357 A1 | 10/2006 | Littrup |
| 2006/0247611 A1 | 11/2006 | Abboud |
| 2006/0253114 A1 | 11/2006 | Saadat |
| 2008/0119836 A1 | 5/2008 | Littrup |
| 2008/0312644 A1 | 12/2008 | Fourkas |
| 2009/0118723 A1 | 5/2009 | Lalonde |
| 2010/0057063 A1 | 3/2010 | Arless |
| 2010/0256621 A1* | 10/2010 | Babkin .......... A61B 18/02 606/21 |
| 2011/0009854 A1 | 1/2011 | Babkin |
| 2011/0040297 A1 | 2/2011 | Babkin |
| 2011/0054453 A1 | 3/2011 | Lalonde |
| 2011/0162390 A1 | 7/2011 | Littrup |
| 2011/0184399 A1 | 7/2011 | Wittenberger |
| 2012/0053575 A1 | 3/2012 | Babkin et al. |
| 2012/0059364 A1 | 3/2012 | Baust |
| 2012/0109118 A1 | 5/2012 | Lalonde |
| 2012/0209257 A1 | 8/2012 | Van Der Weide et al. |
| 2012/0253336 A1 | 10/2012 | Littrup |
| 2013/0073014 A1 | 3/2013 | Lim |
| 2013/0197498 A1 | 8/2013 | Laske |
| 2013/0204241 A1 | 8/2013 | Baust |
| 2013/0324987 A1 | 12/2013 | Leung |
| 2013/0331829 A1 | 12/2013 | Babkin |
| 2013/0345688 A1 | 12/2013 | Babkin |
| 2014/0350537 A1* | 11/2014 | Baust .......... A61B 18/02 606/25 |
| 2014/0364848 A1 | 12/2014 | Heimbecher |
| 2015/0250524 A1 | 9/2015 | Moriarty |

FOREIGN PATENT DOCUMENTS

| | | |
|---|---|---|
| JP | 7-136180 | 5/1995 |
| JP | 2008-515469 | 5/2008 |
| WO | WO1993008751 | 5/1993 |
| WO | WO1997049344 | 12/1997 |
| WO | WO2002058576 | 8/2002 |
| WO | WO2002096270 | 12/2002 |
| WO | WO2002011638 | 4/2003 |
| WO | 2004/064914 | 8/2004 |
| WO | WO2004064914 | 3/2005 |
| WO | 2006137887 A2 | 12/2006 |
| WO | 2009/009398 | 1/2009 |
| WO | WO2009067497 | 5/2009 |
| WO | WO2013013098 | 1/2013 |
| WO | WO2013013099 | 1/2013 |
| WO | WO2015160574 | 10/2015 |

OTHER PUBLICATIONS

International Search Report dated Mar. 18, 2015 for PCT/US14/56839.
International Search Report dated Jan. 21, 2015 for PCT/US2014/059684.
International Search Report dated Oct. 1, 2012 for PCT/US2012/047487.
International Search Report /Written Opinion dated Jan. 14, 2009 for PCT/US2008/084004.
European Search Report for EP04702597 dated Sep. 18, 2007.
European Search Report for EP08852254 dated Nov. 19, 2010.
European Search Report for EP05858178.6 dated Nov. 5, 2010.
European Search Report for EP10184565 dated Feb. 21, 2011.
Arai, Y., et al., "Supercritical Fluids," pp. 161 and 199, ISBN 3540412484, Springer 2002.
Barron, randall F., "Cryogenic Heat Transfer," pp. 97, 129 and 130, Taylor & Francis, 1999.
Lide, D.R. and Keihiaian, H.V., "CRC Handbook of Thermophysical and Thermochemical Data," p. 375, CRC Press 1994.
Sun, Ya-ping, Supercritical Fluid Technology in Materials Science and Engineering, pp. 1 and 26, CRC Press 2002.
Thakore, S.B. and Bhatt, B.I., "Introduction to Process Engineering and Design," Chemical Engineering Series, pp. 27-28, McGraw-Hill 2008.
Office Action dated Jul. 26, 2018 for U.S. Appl. No. 14/915,631.
Office Action dated Jul. 13, 2018 for U.S. Appl. No. 15/028,925.
Supplemental European Search Report dated Apr. 23, 2018 for EP15858716.
Australian Examination Report No. 1, dated Jul. 31, 2018 for 2014327045.
Stuehlinger, M., et al., "CoolLoop First: A First in Man Study to Test a Novel Circular Cryoablation System in Paroxysmal Artial Fibrillation," Journal of Artial Fibrillation, vol. 81, Issue 3, Oct.-Nov. 2015.
Skanes, Allan C., et al., "Cryoblation: Potentials and Pitfalls," doi:10.1046/j.1540-8167.2004.15106.x, Jul. 6, 2004.
Lemola, Kristina, MD, et al., "Pulmonary Vein Isolation as an End Point for Left Atrial Circumferential Ablation of Atrial Fibrillation," Journal of American College of Cardiology, vol. 46, No. 6, 2005.
Rolf, Sascha, MD, et al., "Electroanatomical Mapping of Atrial Fibrillation: Review of the Current Techniques and Advances," Journal of Artrial Fibrillation, vol. 7, Issue 4, Dec. 2014-Jan. 2015.
International Search Report dated Dec. 28, 2016 for PCT/US2016/033833.
International Search Report dated Jan. 31, 2017 for PCT/US2016/051954.
International Search Report dated Feb. 2, 2017 for PCT/US2016/063882.
International Search Report dated Jan. 15, 2016 for PCT/US2015/056780.

* cited by examiner

PRESSURE MODULATED CRYOABLATION SYSTEM AND RELATED METHODS

CROSS REFERENCE TO RELATED APPLICATIONS

This application claims the benefit of U.S. Provisional Patent Application No. 62/079,299, filed on Nov. 13, 2014, and is incorporated herein by reference.

BACKGROUND OF THE INVENTION

1. Field of the Invention

This invention relates to cryosurgery and more particularly to cryoablation catheters comprising a fluid operating near its critical point.

2. Description of the Related Art

Cryoablation is a surgical technique for ablating tissue by cooling or freezing the tissue to a lethal degree. Cryoablation has the benefit of minimizing permanent collateral tissue damage and has applicability to a wide range of therapies including the treatment of cancer and heart disease.

A shortcoming with certain cryosurgical systems, however, arises from the process of evaporation. The process of evaporation of a liquefied gas results in enormous expansion as the liquid converts to a gas; the volume expansion is on the order of a factor of 200. In a small-diameter system, this degree of expansion consistently results in a phenomenon known in the art as "vapor lock." The phenomenon is exemplified by the flow of a cryogen in a thin-diameter tube. The formation of a relatively massive volume of expanding gas impedes the forward flow of the liquid cryogen through the tubes.

Traditional techniques that have been used to avoid vapor lock have included restrictions on the diameter of the tube, requiring that it be sufficiently large to accommodate the evaporative effects that lead to vapor lock. Other complex cryo-apparatus and tubing configurations have been used to "vent" $N_2$ gas as it is formed along transport tubing. These designs also contributed to limiting the cost efficacy and tube diameter.

There is accordingly a need for improved methods and systems for providing minimally invasive, safe and efficient cryogenic cooling of tissues.

SUMMARY OF THE INVENTION

An endovascular near critical fluid based cryoablation system for creating a lesion in tissue comprises a near critical fluid pressure source or generator; a near critical fluid cooler for cooling the near critical fluid; a near critical fluid based cryoablation catheter in fluid communication with the generator; and a controller operable to control the cooling power delivered from a distal treatment section of the catheter to the tissue to cool the tissue. The controller adjusts the pressure from a relatively high (for example, near critical) pressure to a substantially lower pressure based on a condition during the catheter activation.

In embodiments, the pressure is modulated based on the temperature of the catheter. When the temperature of the catheter reaches a target temperature, the pressure is reduced.

The description, objects and advantages of the present invention will become apparent from the detailed description to follow, together with the accompanying drawings.

DETAILED DESCRIPTION OF THE INVENTION

Before the present invention is described in detail, it is to be understood that this invention is not limited to particular variations set forth herein as various changes or modifications may be made to the invention described and equivalents may be substituted without departing from the spirit and scope of the invention. As will be apparent to those of skill in the art upon reading this disclosure, each of the individual embodiments described and illustrated herein has discrete components and features which may be readily separated from or combined with the features of any of the other several embodiments without departing from the scope or spirit of the present invention. In addition, many modifications may be made to adapt a particular situation, material, composition of matter, process, process act(s) or step(s) to the objective(s), spirit or scope of the present invention. All such modifications are intended to be within the scope of the claims made herein.

Methods recited herein may be carried out in any order of the recited events which is logically possible, as well as the recited order of events. Furthermore, where a range of values is provided, it is understood that every intervening value, between the upper and lower limit of that range and any other stated or intervening value in that stated range is encompassed within the invention. Also, it is contemplated that any optional feature of the inventive variations described may be set forth and claimed independently, or in combination with any one or more of the features described herein.

All existing subject matter mentioned herein (e.g., publications, patents, patent applications and hardware) is incorporated by reference herein in its entirety except insofar as the subject matter may conflict with that of the present invention (in which case what is present herein shall prevail).

Embodiments of the invention make use of thermodynamic processes using cryogens that provide cooling without encountering the phenomenon of vapor lock.

Cryogen Phase Diagram and near Critical Point

Figure 1:
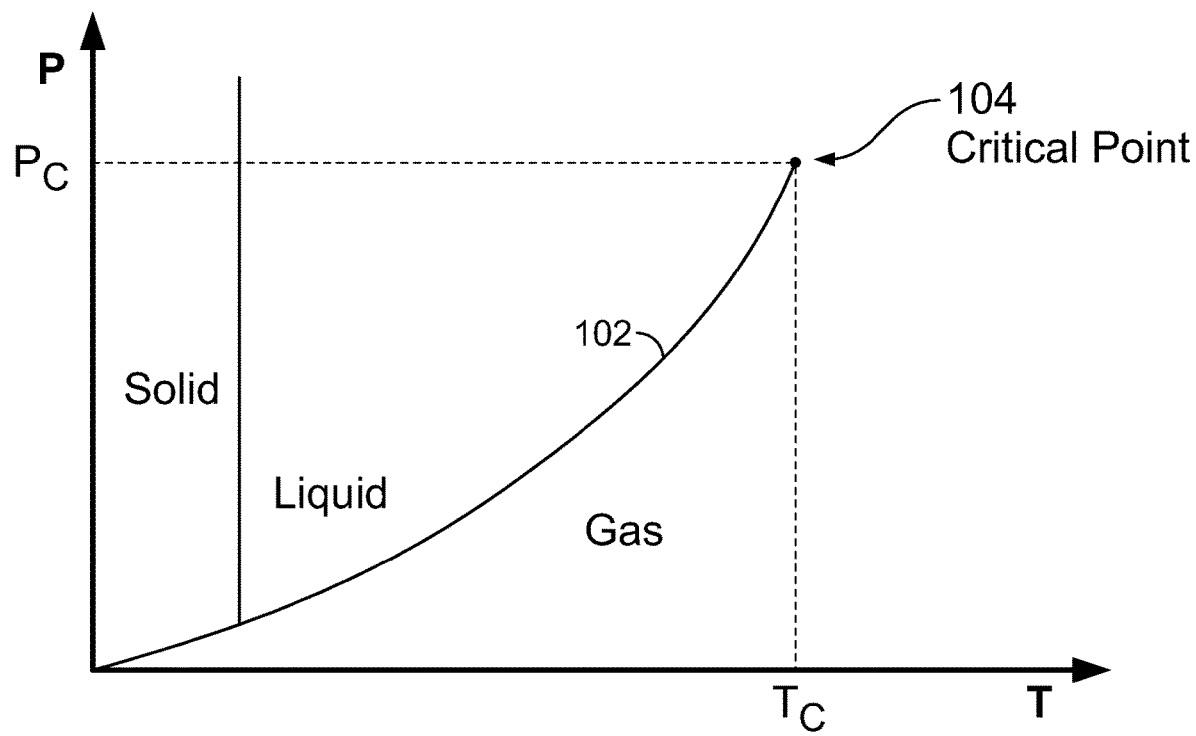
FIG. 1 illustrates a typical cryogen phase diagram.

This application uses phase diagrams to illustrate and compare various thermodynamic processes. An example phase diagram is shown in FIG. 1. The axes of the diagram correspond to pressure P and temperature T, and includes a phase line 102 that delineates the locus of all (P, T) points where liquid and gas coexist. For (P, T) values to the left of the phase line 102, the cryogen is in a liquid state, generally achieved with higher pressures and lower temperatures, while (P, T) values to the right of the phase line 102 define regions where the cryogen is in a gaseous state, generally achieved with lower pressures and higher temperatures. The phase line 102 ends abruptly in a single point known as the critical point 104. In the case of nitrogen $N_2$, the critical point is at $P_c=3.396$ MPa and $T_c=-147.15°$ C.

When a fluid has both liquid and gas phases present during a gradual increase in pressure, the system moves up along the liquid-gas phase line 102. In the case of $N_2$, the liquid at low pressures is up to two hundred times more dense than the gas phase. A continual increase in pressure causes the density of the liquid to decrease and the density of the gas phase to increase, until they are equal only at the critical point 104. The distinction between liquid and gas disappears at the critical point 104. The blockage of forward flow by gas expanding ahead of the liquid cryogen is thus avoided by conditions surrounding the critical point, defined herein as "near-critical conditions." Factors that allow greater departure from the critical point while maintaining a functional flow include greater speed of cryogen flow, larger diameter of the flow lumen and lower heat load upon the thermal exchanger, or cryo treatment region tip.

As the critical point is approached from below, the vapor phase density increases and the liquid phase density decreases until right at the critical point, where the densities of these two phases are exactly equal. Above the critical point, the distinction of liquid and vapor phases vanishes, leaving only a single, supercritical phase. All gases obey quite well the following van der Waals equation of state:

$$(p+3/v^2)(3v-1)=8t \qquad [\text{Eq. 1}]$$

where $p=P/P_c$, $v=V/V_c$, and $t=T/T_c$, and $P_c$, $V_c$, and $T_c$ are the critical pressure, critical molar volume, and the critical temperature respectively.

The variables v, p, and t are often referred to as the "reduced molar volume," the "reduced pressure," and the "reduced temperature," respectively. Hence, any two substances with the same values of p, v, and t are in the same thermodynamic state of fluid near its critical point. Eq. 1 is thus referred to as embodying the "Law of Corresponding States." This is described more fully in H. E. Stanley, *Introduction to Phase Transitions and Critical Phenomena* (Oxford Science Publications, 1971), the entire disclosure of which is incorporated herein by reference for all purposes.

In embodiments of the invention, the reduced pressure p is fixed at a constant value of approximately one, and hence at a fixed physical pressure near the critical pressure, while the reduced temperature t varies with the heat load applied to the device. If the reduced pressure p is a constant set by the engineering of the system, then the reduced molar volume v is an exact function of the reduced temperature t.

In other embodiments of the invention, the operating pressure p may be adjusted so that over the course of variations in the temperature t of the device, v is maintained below some maximum value at which the vapor lock condition will result. It is generally desirable to maintain p at the lowest value at which this is true since boosting the pressure to achieve higher values of p may involve use of a more complex and more expensive compressor, resulting in more expensive procurement and maintenance of the entire apparatus support system and lower overall cooling efficiency.

The conditions that need to be placed on v depend in a complex and non-analytic way on the volume flow rate dV/dt, the heat capacity of the liquid and vapor phases, and the transport properties such as the thermal conductivity, viscosity, etc., in both the liquid and the vapor. This exact relationship is not derived here in closed form algebraically, but may be determined numerically by integrating the model equations that describe mass and heat transport within the device. Conceptually, vapor lock occurs when the rate of heating of the needle (or other device structure for transporting the cryogen and cooling the tissue) produces the vapor phase. The cooling power of this vapor phase, which is proportional to the flow rate of the vapor times its heat capacity divided by its molar volume, is not able to keep up with the rate of heating to the needle. When this occurs, more and more of the vapor phase is formed in order to absorb the excess heat through the conversion of the liquid phase to vapor in the cryogen flow. This creates a runaway condition where the liquid converts into vapor phase to fill the needle, and effectively all cryogen flow stops due to the large pressure that results in this vapor phase as the heat flow into the needle increases its temperature and pressure rapidly. This condition is called "vapor lock."

In accordance with one embodiment of the present invention, the liquid and vapor phases are substantially identical in their molar volume. The cooling power is at the critical point, and the cooling system avoids vapor lock. Additionally, at conditions slightly below the critical point, the apparatus may avoid vapor lock as well.

Cryoablation Systems

Figure 2:
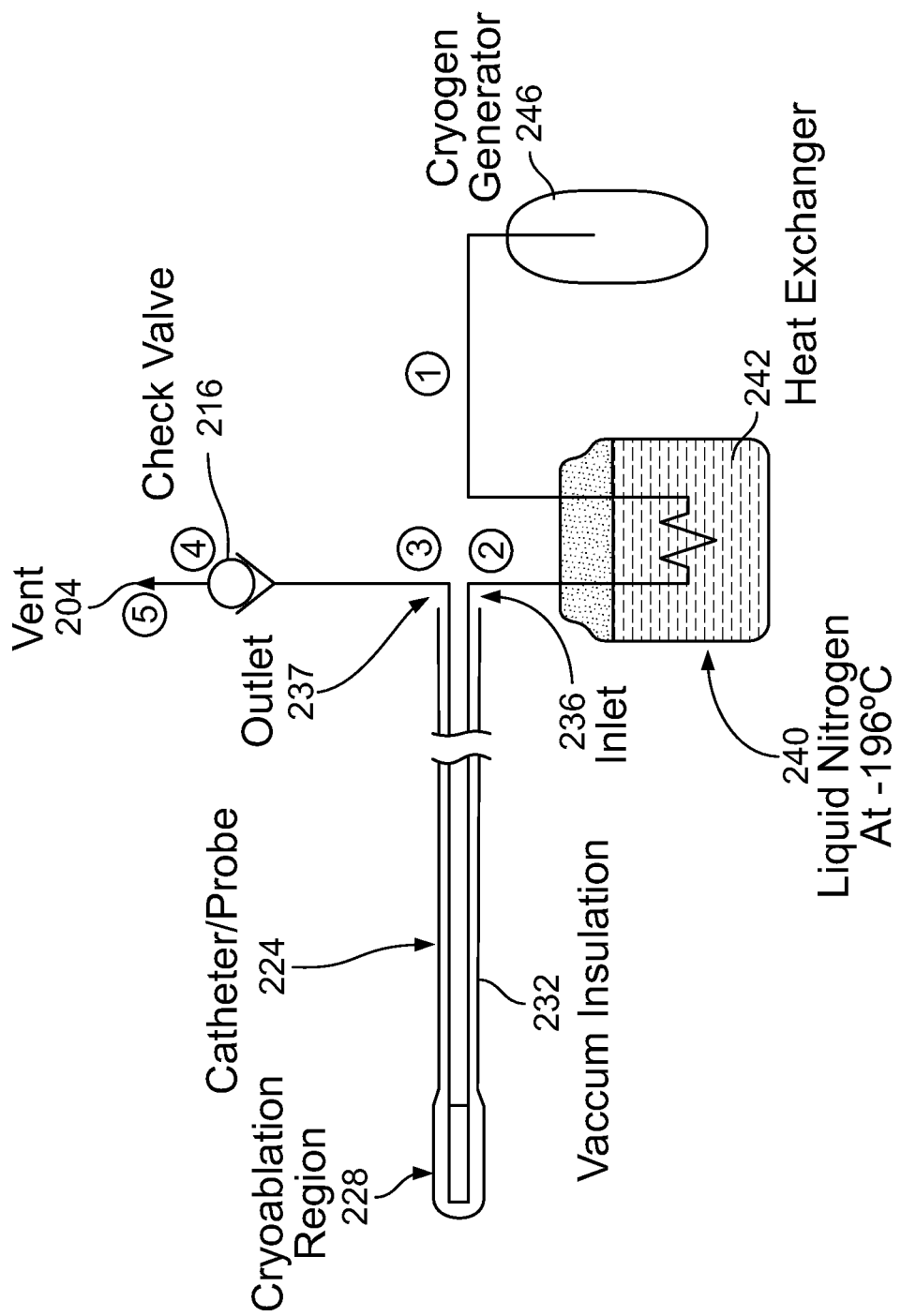
FIG. 2 is a schematic illustration of a cryogenic cooling system.
Figure 3:
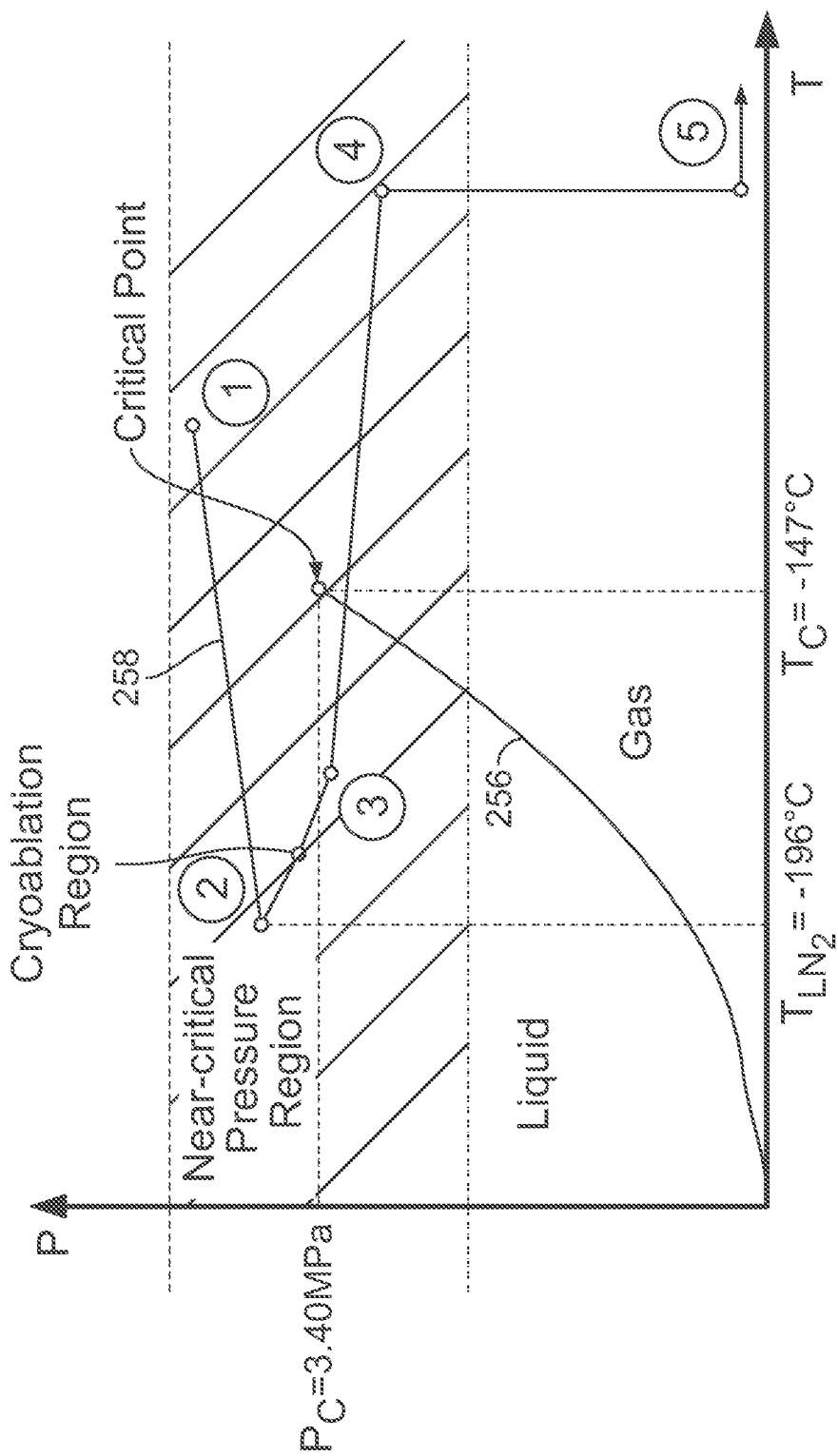
FIG. 3 is a cryogen phase diagram corresponding to the system shown in FIG. 2.

FIG. 2 provides a schematic illustration of a structural arrangement for a cryogenic system in one embodiment, and FIG. 3 provides a phase diagram that illustrates a thermodynamic path taken by the cryogen when the system of FIG. 2 is operated. The circled numerical identifiers in the two figures correspond so that a physical position is indicated in FIG. 2 where operating points identified along the thermodynamic path are achieved. The following description thus sometimes makes simultaneous reference to both the structural drawing of FIG. 2 and to the phase diagram of FIG. 3 in describing physical and thermodynamic aspects of the cooling flow.

For purposes of illustration, both FIGS. 2 and 3 make specific reference to a nitrogen cryogen, but this is not intended to be limiting. The invention may more generally be used with any suitable cryogen such as, for example, argon, neon, helium, hydrogen, and oxygen.

In FIG. 3, the liquid-gas phase line is identified with reference label 256 and the thermodynamic path followed by the cryogen is identified with reference label 258.

A cryogenic generator 246 is used to supply the cryogen at a pressure that exceeds the critical-point pressure $P_c$ for the cryogen at its outlet, referenced in FIGS. 2 and 3 by label ①. The cooling cycle may generally begin at any point in the phase diagram having a pressure above or slightly below $P_c$, although it is advantageous for the pressure to be near the critical-point pressure $P_c$. The cooling efficiency of the process described herein is generally greater when the initial pressure is near the critical-point pressure Pc so that at higher pressures there may be increased energy requirements to achieve the desired flow. Thus, embodiments may sometimes incorporate various higher upper boundary pressure but generally begin near the critical point, such as between 0.8 and 1.2 times $P_c$, and in one embodiment at about 0.85 times $P_c$.

As used herein, the term "near critical" is meant to refer to near the liquid-vapor critical point. Use of this term is equivalent to "near a critical point" and it is the region where the liquid-vapor system is adequately close to the critical point, where the dynamic viscosity of the fluid is close to that of a normal gas and much less than that of the liquid; yet, at the same time its density is close to that of a normal liquid state. The thermal capacity of the near critical fluid is even greater than that of its liquid phase. The combination of gas-like viscosity, liquid-like density and very large thermal capacity makes it a very efficient cooling agent. Reference to a near critical point refers to the region where the liquid-vapor system is adequately close to the critical point so that the fluctuations of the liquid and vapor phases are large enough to create a large enhancement of the heat capacity over its background value. The near critical temperature is a temperature within ±10% of the critical point temperature. The near critical pressure is between 0.8 and 1.2 times the critical point pressure.

Referring again to FIG. 2, the cryogen is flowed through a tube, at least part of which is surrounded by a reservoir 240 of the cryogen in a liquid state, reducing its temperature without substantially changing its pressure. In FIG. 2, reservoir is shown as liquid $N_2$, with a heat exchanger 242 provided within the reservoir 240 to extract heat from the flowing cryogen. Outside the reservoir 240, thermal insulation may be provided around the tube to prevent unwanted warming of the cryogen as it is flowed from the cryogen generator 246. At point ②, after being cooled by being brought into thermal contact with the liquid cryogen, the cryogen has a lower temperature but is at substantially the initial pressure. In some instances, there may be a pressure change, as is indicated in FIG. 3 in the form of a slight pressure decrease, provided that the pressure does not drop substantially below the critical-point pressure $P_c$, i.e. does not drop below the determined minimum pressure. In the example shown in FIG. 3, the temperature drop as a result of flowing through the liquid cryogen is about 50° C.

The cryogen is then provided to a device for use in cryogenic applications. In the exemplary embodiment shown in FIG. 2, the cryogen is provided to an inlet 236 of a catheter 224, such as may be used in medical cryogenic endovascular applications, but this is not a requirement.

Indeed, the form of the medical device may vary widely and include without limitation: instruments, appliances, catheters, devices, tools, apparatus', and probes regardless of whether such probe is short and rigid, or long and flexible, and regardless of whether it is intended for open, minimal, non-invasive, manual or robotic surgeries.

In embodiments, the cryogen may be introduced through a proximal portion of a catheter, continue along a flexible intermediate section of the catheter, and into the distal treatment section of the catheter. As the cryogen is transported through the catheter, and across the cryoablation treatment region 228, between labels ② and ③ in FIGS. 2 and 3, there may be a slight change in pressure and/or temperature of the cryogen as it moves through the interface with the device, e.g. cryoablation region 228 in FIG. 2. Such changes may typically show a slight increase in temperature and a slight decrease in pressure. Provided the cryogen pressure remains above the determined minimum pressure (and associated conditions), slight increases in temperature do not significantly affect performance because the cryogen simply moves back towards the critical point without encountering the liquid-gas phase line 256, thereby avoiding vapor lock.

Thermal insulation along the shaft of the cryotherapy catheter (or apparatus, appliance, needle, probe, etc.) and along the support system that delivers near-critical freeze capability to these needles may use a vacuum.

Flow of the cryogen from the cryogen generator 246 through the catheter 224 or other device may be controlled in the illustrated embodiment with an assembly that includes a check valve 216, a flow impedance, and/or a flow controller. The catheter 224 itself may comprise a vacuum insulation 232 (e.g., a cover or jacket) along its length and may have a cold cryoablation region 228 that is used for the cryogenic applications. Unlike a Joule-Thomson probe, where the pressure of the working cryogen changes significantly at the probe tip, these embodiments of the invention provide relatively little change in pressure throughout the apparatus. Thus, at point ④, the temperature of the cryogen has increased approximately to ambient temperature, but the pressure remains elevated. By maintaining the pressure above or near the critical-point pressure $P_c$ as the cryogen is transported through the catheter, the liquid-gas phase line 256 and vapor lock are avoided.

The cryogen pressure returns to ambient pressure at point ⑤. The cryogen may then be vented through vent 204 at substantially ambient conditions.

Examples of near critical fluid cryoablation systems, their components, and various arrangements are described in U.S. patent application Ser. No. 10/757,768 which issued as U.S. Pat. No. 7,410,484, on Aug. 12, 2008 entitled "CRYOTHERAPY PROBE", filed Jan. 14, 2004 by Peter J. Littrup et al.; U.S. patent application Ser. No. 10/757,769 which issued as U.S. Pat. No. 7,083,612 on Aug. 1, 2006, entitled "CRYOTHERAPY SYSTEM", filed Jan. 14, 2004 by Peter J. Littrup et al.; U.S. patent application Ser. No. 10/952,531 which issued as U.S. Pat. No. 7,273,479 on Sep. 25, 2007 entitled "METHODS AND SYSTEMS FOR CRYOGENIC COOLING" filed Sep. 27, 2004 by Peter J. Littrup et al. and U.S. Pat. No. 8,387,402 to Littrup et al., all of which are incorporated herein by reference, in their entireties, for all purposes.

Figure 4:
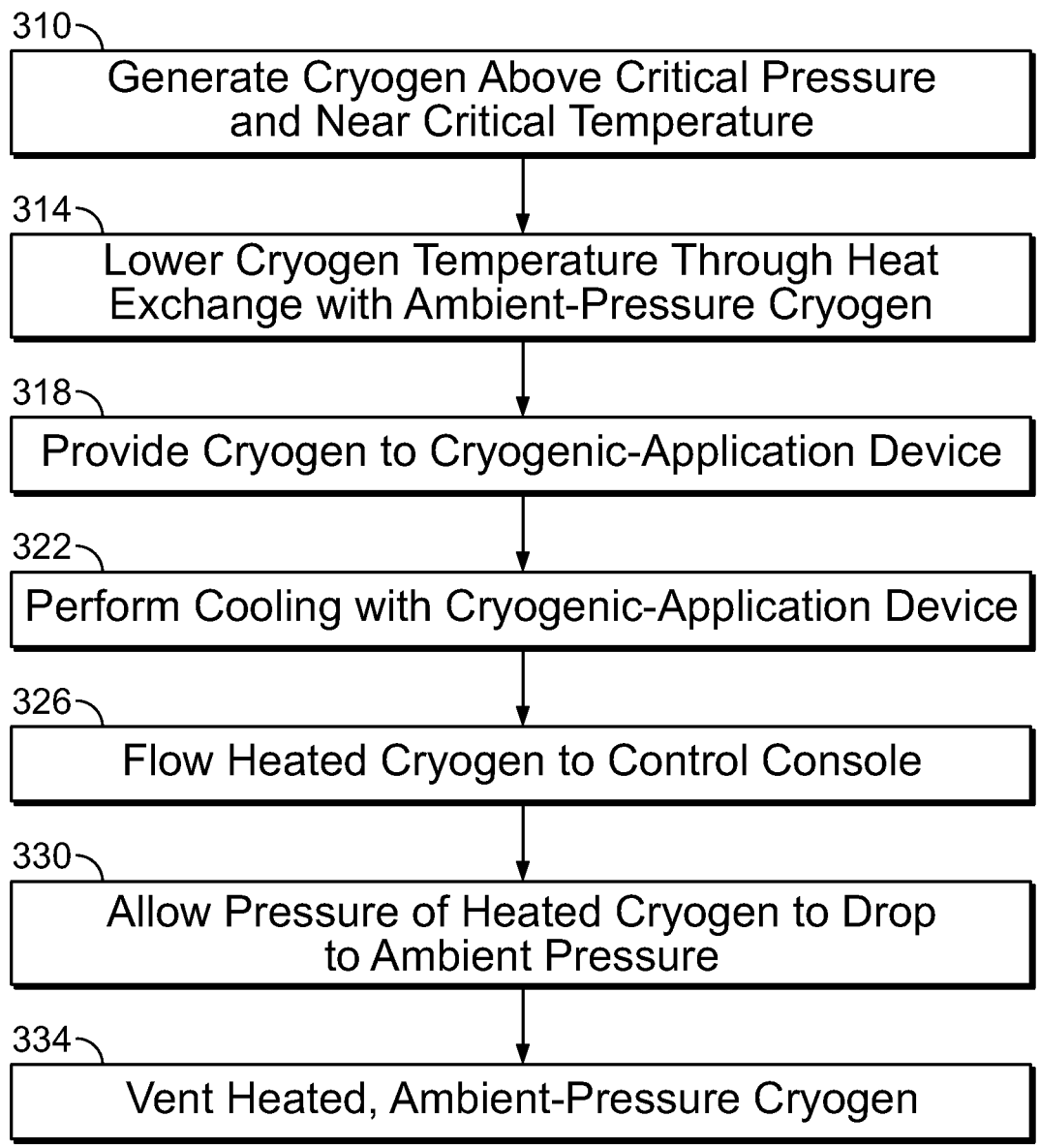
FIG. 4 provides a flow diagram that summarizes aspects of the cooling method of FIG. 2.

A method for cooling a target tissue in which the cryogen follows a thermodynamic path similar to that shown in FIG. 3 is illustrated with the flow diagram of FIG. 4. At block 310, the cryogen is generated with a pressure that exceeds the critical-point pressure and is near the critical-point temperature. The temperature of the generated cryogen is lowered at block 314 through heat exchange with a substance having a lower temperature. In some instances, this may conveniently be performed by using heat exchange with an ambient-pressure liquid state of the cryogen, although the heat exchange may be performed under other conditions in different embodiments. For instance, a different cryogen might be used in some embodiments, such as by providing heat exchange with liquid nitrogen when the working fluid is argon. Also, in other alternative embodiments, heat exchange may be performed with a cryogen that is at a pressure that differs from ambient pressure, such as by providing the cryogen at lower pressure to create a colder ambient.

The further cooled cryogen is provided at block 318 to a cryogenic-application device, which may be used for a cooling application at block 322. The cooling application may comprise chilling and/or freezing, depending on whether an object is frozen with the cooling application. The temperature of the cryogen is increased as a result of the cryogen application, and the heated cryogen is flowed to a control console at block 326. While there may be some variation, the cryogen pressure is generally maintained greater than the critical-point pressure throughout blocks 310-326; the principal change in thermodynamic properties of the cryogen at these stages is its temperature. At block 330, the pressure of the heated cryogen is then allowed to drop to ambient pressure so that the cryogen may be vented, or recycled, at block 334. In other embodiments, the remaining pressurized cryogen at block 326 may also return along a path to block 310 to recycle rather than vent the cryogen at ambient pressure.

Pressure Modulation

Figure 5:
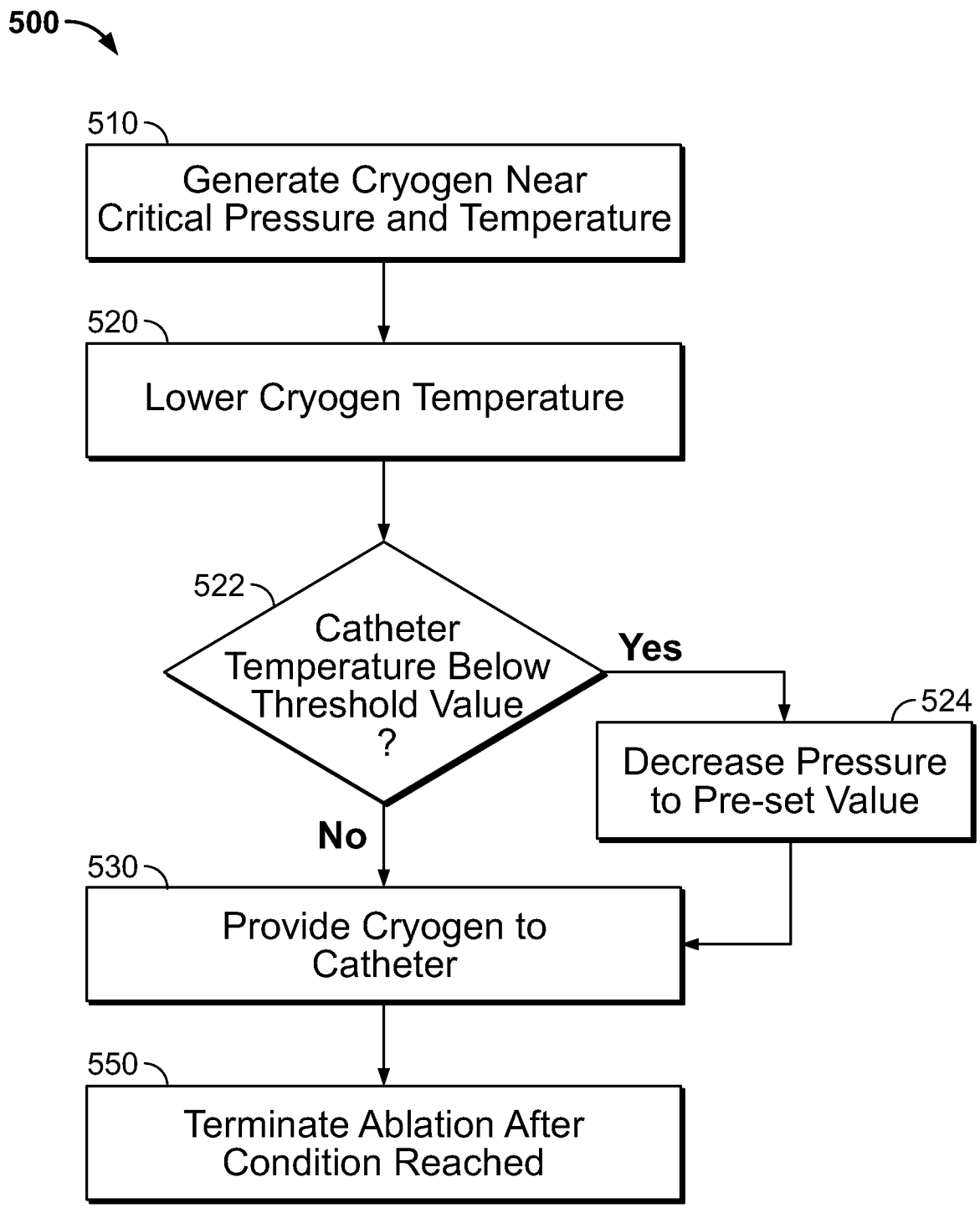
FIG. 5 is a flow diagram that summarizes aspects of another cooling method.

FIG. 5 is a flow diagram 500 illustrating another embodiment of the invention.

Step 510 recites to generate cryogen at or near critical pressure and temperature. Step 510 may be carried out, for example, as described above with reference to FIGS. 2-3.

Step 520 recites to lower the cryogen temperature. Step 520 may also be carried out, for example, as described above with reference to FIGS. 2-3

Step 522 recites to determine whether the catheter temperature is below a threshold value. Temperature measurement may be performed using thermocouples placed on the end of the treatment section, or within the transport channels or otherwise along the flow path so as to measure temperature of the apparatus itself, the cryogen, and/or the tissue. Indeed a plurality of temperature sensors may be placed throughout the tip, treatment section, the inlet flowpath, the return flowpath, and preferably, in direct contact with the cryogen to obtain an accurate measurement of real time temperature, temperature change over time, and temperature difference of the incoming cryogen versus the outgoing cryogen.

If the temperature is not below a threshold value, the pressure is not reduced.

If the temperature is below a threshold value, then the pressure is decreased to a pre-set value as indicated by step 524. In embodiments, after the cryo apparatus treatment section is placed adjacent the target tissue to be cooled, and the temperature is confirmed to be below a threshold value, the pressure is substantially reduced from the first relatively high (near critical) pressure to a second lower pressure once the apparatus tip or tissue reaches a target temperature.

Subsequent to determining whether the temperature is below a pre-set value and whether to reduce the pressure, step 530 recites to provide cryogen to a catheter. Step 530 may also be carried out, for example, as described above with reference to FIGS. 2-3.

Without being bound by theory, once the catheter freezing element or tissue temperature is lowered to a target cold temperature (for example, −100 degrees C.), the above mentioned problem associated with vapor lock is minimized because the tissue surrounding the apparatus' treatment section is lowered (namely, frozen). The chilled tissue does not act as a heat sink (and warm) the flowing cryogen in the same way that the tissue initially acted as a heat sink to warm the cryogen. The cryogen shall not have a tendency to transform from a liquid phase to vapor phase within the apparatus. The cryogen is anticipated to remain as a liquid, and the gas molar volume does not increase during the flow cycle. Consequently, the embodiment described in FIG. 5 provides an initial (or first) high pressure phase of cryogen operation, and a second low-pressure treatment phase. Exemplary pressures during the low pressure treatment phase range from 200 to 0 psi and temperatures in the range of −50 to −150 degrees C. Additionally, the time period for the initial high pressure and lower treatment phases range from 10 seconds to 1 minute, and 30 seconds to 4 minutes respectively.

Figure 6:
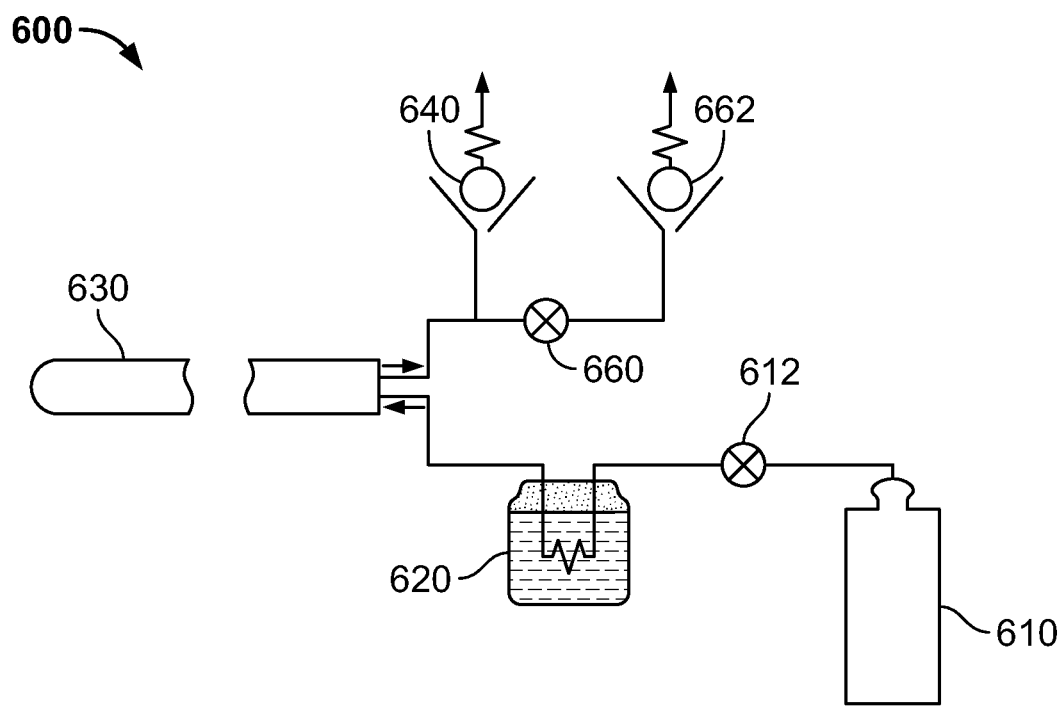
FIG. 6 is a schematic illustration of a cryogenic cooling system comprising a second flow path.
Figure 7:
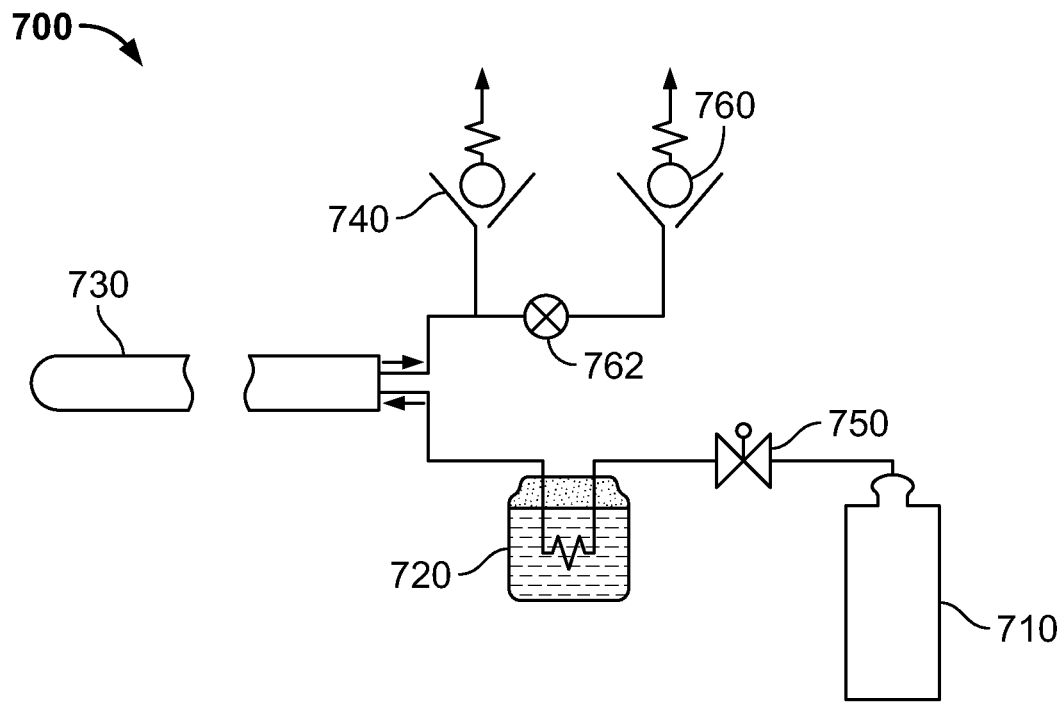
FIG. 7 is a schematic illustration of a cryogenic cooling system comprising a pressure regulator.
Figure 8:
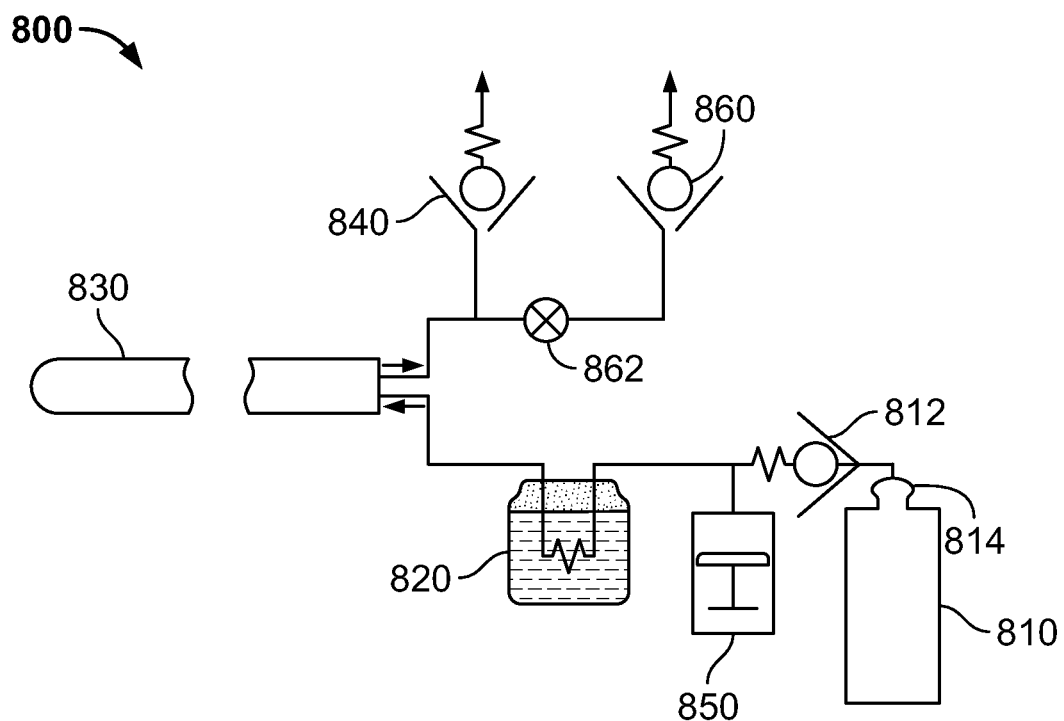
FIG. 8 is a schematic illustration of a cryogenic cooling system comprising a piston or diaphragm.

A wide variety of systems may be employed to modulate the pressure between the high (near critical) pressure to a relatively low pressure. FIGS. 6-8 are schematic diagrams illustrating various cryoablation systems having pressure modulation or adjustment components.

With reference to FIG. 6, for example, a cryoablation system 600 comprises a first cryogen flow path including a high pressure cryogen supply or generator 610, a cooling means 620, a cryoablation catheter 630, and a high pressure check valve 640. Check valve 640 may operate to open at pressures ranging from, e.g., 400 to 480 psi. The first flow path transports the cryogen for a first or initial phase to the treatment section of the catheter preferably under a near critical pressure. Vapor lock is avoided.

After an initial phase, or at which point in time the measured temperature reaches a threshold temperature indicating that the adjacent tissue is substantially cooled, and that the risk of vapor lock is minimized, valve 660 is opened. The cryogen flows to low pressure valve 662, which opens at a second substantially lower pressure than check valve 640. The second low pressure valve may be programmed to open at a pressure ranging from 300 to 0 psi, and more preferably less than or equal to 200 psi. The cryogen may then be further processed, or released to the environment.

The valves described herein may be operated manually or, in embodiments, by using more sophisticated equipment such as a controller. The controller would operate to send signals to the valves and other system components to perform a cryoablation treatment.

The pressure modulated system described herein has both practical and safety advantages over a steady state near critical based cryoablation system. Lower pressure cryogen is easier to work with because there is less energy required to reach the operating pressure, the risk of a leak is less likely at low pressure, the consequences or damage arising from leaks is less with use of a cryogen under a lower pressure. In particular, a leak of a low pressure cryogen would have less impact on equipment, patient safety, and the operator than a leak of high pressure cryogen. Additionally, a low pressure cryogen may be vented directly to the atmosphere.

FIG. 7 illustrates another cryoablation system 700 capable of modulating the pressure. Similar to the system described above, cryoablation system 700 comprises a high pressure cryogen supply or generator 710, a cooling means 720, a cryoablation catheter 730, and a first check valve 740. A first flow path transports the cryogen for a first or initial phase to the treatment section of the catheter preferably under a near critical pressure. Vapor lock is avoided.

Figure 9A:
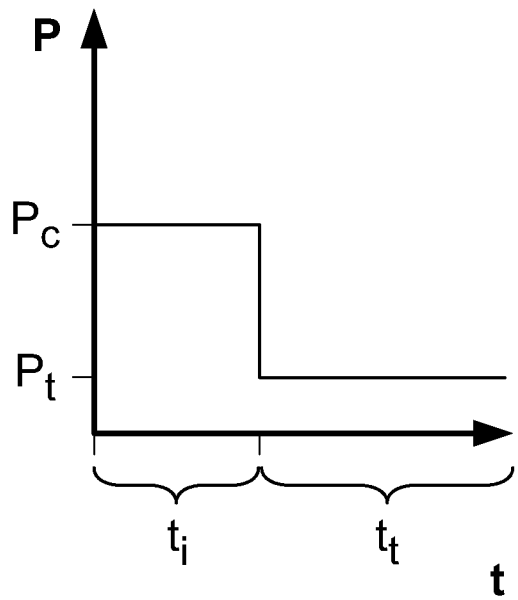
FIGS. 9A-9D are pressure time curves corresponding to various pressure modulated cryogenic cooling systems.
Figure 9B:
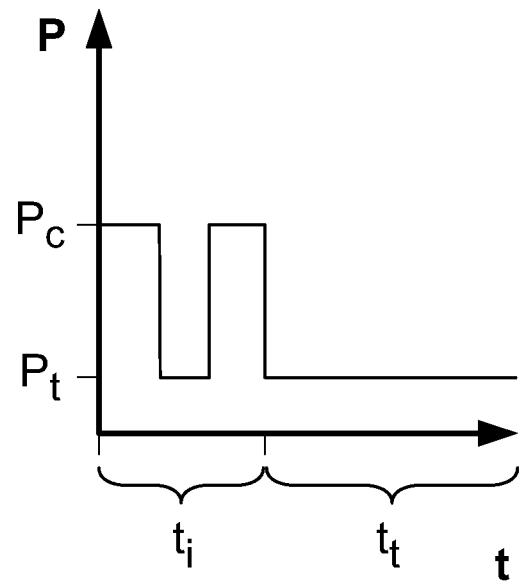

With reference to FIG. 9A, after the initial time period $t_i$, pressure regulator 750 is activated to cause a reduction in the pressure to a second low pressure $P_t$. Consequently, a low pressure cryogen is transported through the cryoablation catheter 730 for treating an adjacent tissue. Vapor lock is avoided despite the reduction in pressure to a pressure substantially below near critical pressure because the instrument end section, and surrounding tissue is cold, and does not cause the cryogen fluid to change phase despite the decrease in pressure.

The pressure regulator and valves may be operated manually or, more preferably, using more sophisticated equipment such as a controller which sends signals to the valves and other system components to perform a cryoablation treatment as described herein.

FIG. 8 illustrates another cryoablation system 800 capable of modulating the pressure. Cryoablation system 800 comprises a cryogen supply 810, one way valve 812, a cooling means 820, a cryoablation catheter 830, and a check valve 840.

Additionally, the system shown in FIG. 8 includes a piston 850 downstream of the one way valve 812. The piston is activated to increase the pressure of the cryogen downstream of the one way valve 812 to a high pressure at or above near critical pressure. Preferably piston is a fast activating member which can increase pressure instantaneously and maintain the desired high pressure for a selected time period. For example, the pressure P may be increased to near critical pressure $P_c$ periodically as shown in plot 9B. As such, the pressure time curve may be defined as a waveform having an amplitude and frequency. The instrument and tissue decrease in temperature towards a lower steady state lethal target temperature. Time period ($t_r$) is representative of a second treatment phase during which the instrument ablation is maintained at the low pressure $P_r$.

Figure 9C:
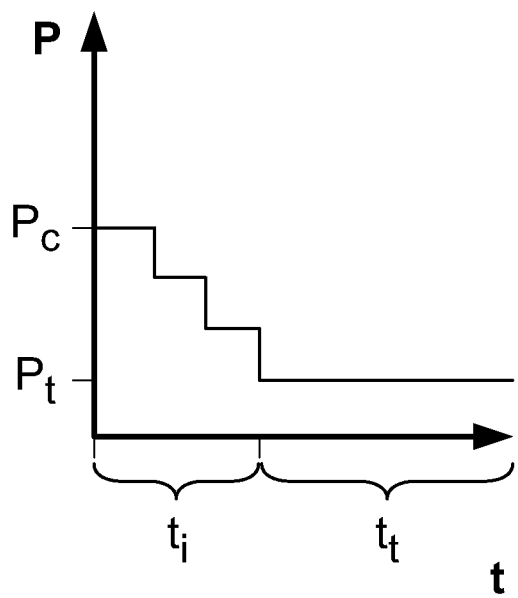

Alternatively, the pressure may be modulated in steps as shown in FIG. 9C. The steps may decrease in equal increments, or non-linearly.

Figure 9D:
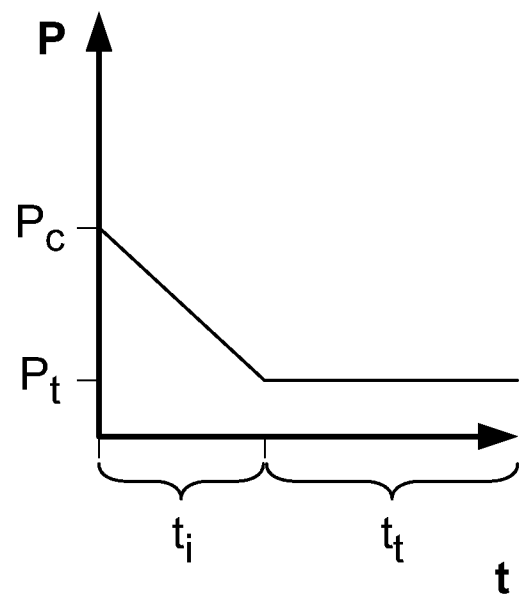

Still in another embodiment, the pressure may be decreased at a continuous rate as shown in FIG. 9D. Although FIG. 9D illustrates a straight profile, the profile may be curved or otherwise ramped towards the low treatment pressure $P_r$.

With reference again to FIG. 8. after the initial phase, piston 850 is deactivated, and valves 814 and 862 are opened. Consequently, a low pressure cryogen is transported through the cryoablation catheter 830 for treating an adjacent tissue. Vapor lock is avoided despite the reduction in pressure to a pressure substantially below near critical pressure because the instrument end section, and surrounding tissue is cold, and does not cause the cryogen fluid to change phase despite the decrease in pressure.

Figure 11:
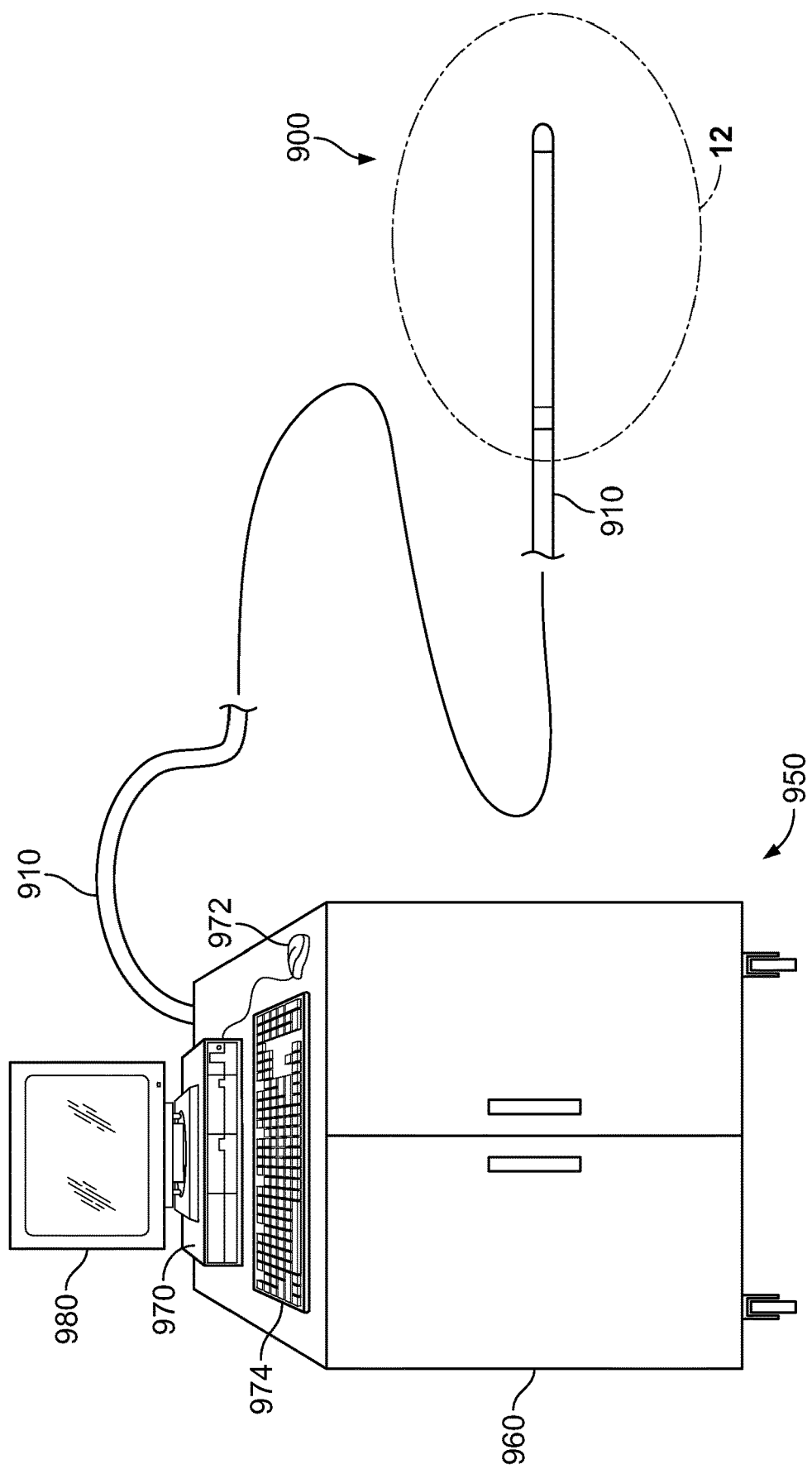
FIG. 11 is an illustration of a cryoablation system including a cryoablation catheter.

As described further herein, the system components (including without limitation the piston, valves, pumps, switches, and regulators) may be activated manually or in other embodiments via a controller. A workstation or console as shown in FIG. 11 and described in the corresponding text may be provided to allow an operator to conveniently operate the cryoablation instrument.

Cryoablation Catheter

Figures 10A, 10B:
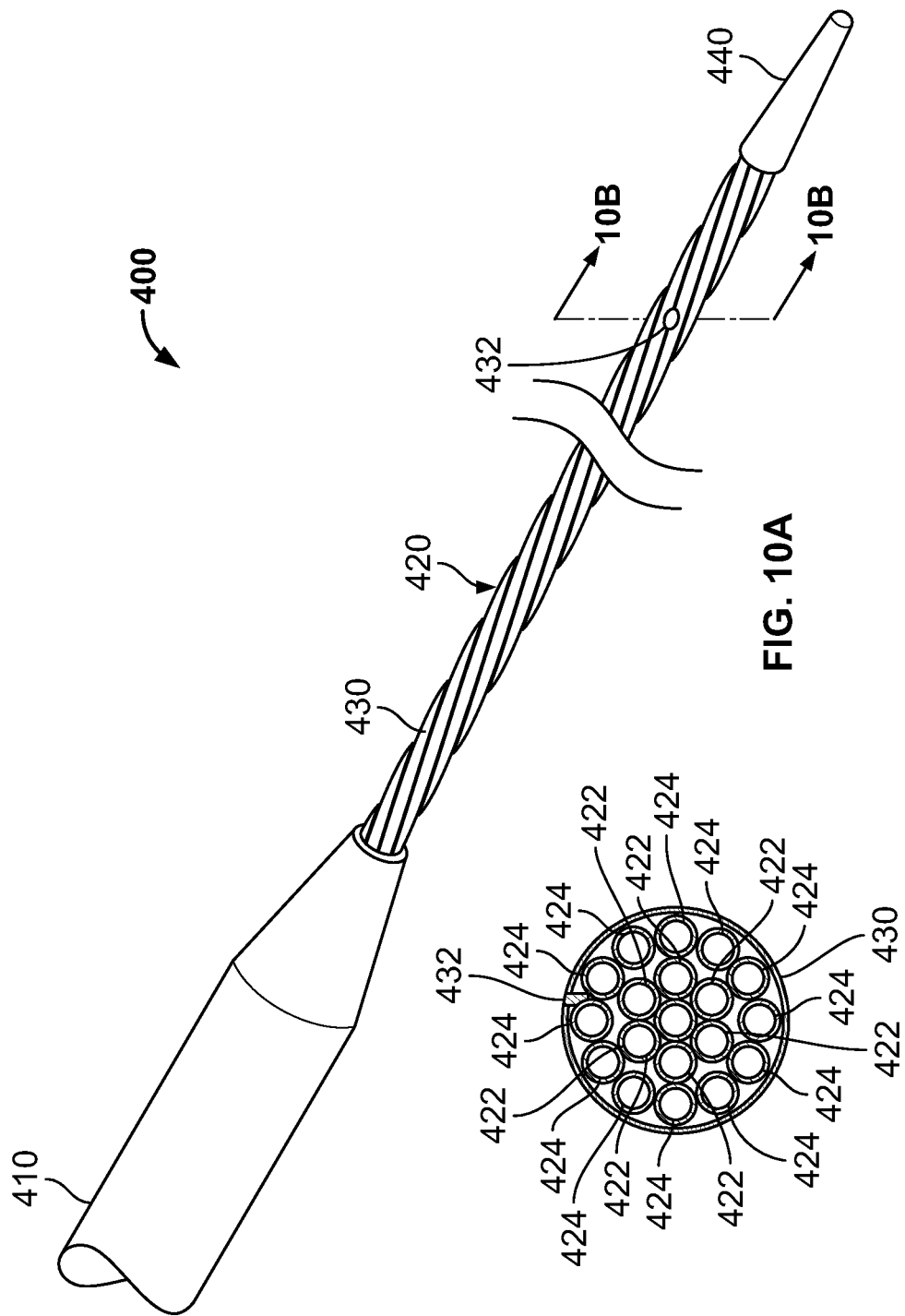
FIG. 10A is a perspective view of a cryoablation catheter.
FIG. 10B is a view taken along line 10B-10B of FIG. 10A.

The cryoablation apparatus of the present invention may have a wide variety of configurations. For example, one embodiment of the present invention is a flexible catheter 400 as shown in FIG. 10A. The catheter 400 includes a proximally disposed housing or connector 410 adapted to fluidly connect to a fluid source (not shown).

A plurality of fluid transfer tubes 420 are shown extending from the connector 410. These tubes include a set of inlet fluid transfer tubes 422 for receiving the inlet flow from the connector and a set of outlet fluid transfer tubes 424 for discharging the outlet flow to the connector 410. In embodiments each of the fluid transfer tubes 422,424 is formed of material that maintains flexibility in a full range of temperatures from −200° C. to ambient temperature. In embodiments, each fluid transfer tube has an inside diameter in a range of between about 0.10 mm and 1.0 mm (preferably between about 0.20 mm and 0.50 mm). Each fluid transfer tube may have a wall thickness in a range of between about 0.01 mm and 0.30 mm (preferably between about 0.02 mm and 0.10 mm).

An end cap 440 is positioned at the ends of the fluid transfer tubes 422, 424 to provide fluid transfer from the inlet fluid transfer tubes 422 to the outlet fluid transfer tubes 424. The endcap is shown having an atraumatic tip. The endcap 440 may be any suitable element for providing fluid transfer from the inlet fluid transfer tubes 422 to the outlet fluid transfer tubes 424. For example, endcap 440 may define an internal chamber, cavity, or passage serving to fluidly connect tubes 422,424.

An outer sheath 430 is also shown in FIG. 10B surrounding the tube bundle 420. The outer sheath serves to hold the tubes in a tubular arrangement, and protect the construct from being penetrated or disrupted by foreign objects and obstacles.

A temperature sensor 432 is shown on the surface of the distal section. Temperature sensor may be a thermocouple to sense a temperature corresponding to the adjacent tissue, and sends the signal back through a wire in the tube bundle to the console for processing. Temperature sensor may be placed elsewhere along the shaft or within one or more of the fluid transport tubes to determine a temperature difference between inflow and outflow.

In embodiments, the fluid transfer tubes 420 are formed of annealed stainless steel or a polymer such as polyimide. In such configurations, the material may maintain flexibility at near critical temperature. In other embodiments, the transfer tube is shape-forming, deflectable, or steerable to make continuous firm contact with various anatomies. Other suitable device designs including deflectable designs are described in international patent application PCT/US2015/024778, filed Apr. 7, 2015, entitled Endovascular Near Critical Fluid Based Cryoablation Catheter Having Plurality of Preformed Treatment Shapes.

There are many configurations for tube arrangements. In embodiments the fluid transfer tubes are formed of a circular array, wherein the set of inlet fluid transfer tubes comprises at least one inlet fluid transfer tube defining a central region of a circle and wherein the set of outlet fluid transfer tubes comprises a plurality of outlet fluid transfer tubes spaced about the central region in a circular pattern. In the configuration shown in FIG. 10B, the fluid transfer tubes 422,424 fall within this class of embodiments.

During operation, the cryogen fluid arrives at the catheter through a supply line from a suitable cryogen source at a temperature close to −200° C. The cryogen is circulated through the multi-tubular freezing zone provided by the exposed fluid transfer tubes, and returns to the connector.

In embodiments, the nitrogen flow does not form gaseous bubbles inside the small diameter tubes under any heat load, so as to not create a vapor lock that limits the flow and the cooling power. By operating at the near critical condition for at least an initial period of energy application, the vapor lock is eliminated as the distinction between the liquid and gaseous phases disappears.

A multi-tubular design may be preferably to a single tube design because the additional tubes can provide a substantial increase in the heat exchange area between the cryogen and tissue. Depending on the number of tubes used, cryo instruments can increase the contact area several times over previous designs having similarly sized diameters with single shafts. However, the invention is not intended to be limited to a single or multi-tube design except where specifically recited in the appended claims.

Cryoablation Console

FIG. 11 illustrates a cryoablation system 950 having a cart or console 960 and a cryoablation catheter 900 detachably connected to the console via a flexible elongate tube 910. The cryoablation catheter 900, which shall be described in more detail below in connection with FIG. 12, contains one or more fluid transport tubes to remove heat from the tissue.

The console 960 may include or house a variety of components (not shown) such as, for example, a generator, controller, tank, valve, pump, etc. A computer 970 and display 980 are shown in FIG. 11 positioned on top of cart for convenient user operation. Computer may include a controller, timer, or communicate with an external controller to drive components of the cryoablation systems such as a pump, valve or generator. Input devices such as a mouse 972 and a keyboard 974 may be provided to allow the user to input data and control the cryoablation devices.

In embodiments computer 970 is configured or programmed to control cryogen flowrate, pressure, and temperatures as described herein. Target values and real time measurement may be sent to, and shown, on the display 980.

Figure 12:
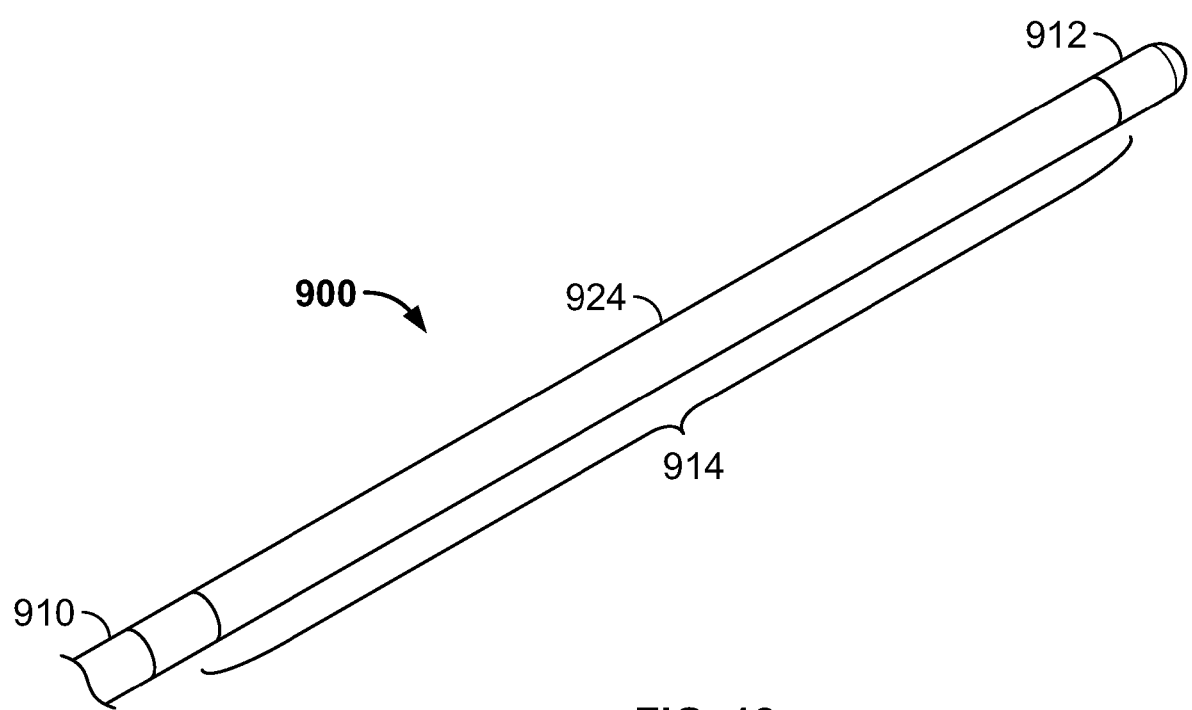
FIG. 12 is an enlarged perspective view of a distal section of the cryoablation catheter shown in FIG. 11.

FIG. 12 shows an enlarged view of distal section of cryoablation apparatus 900. The distal section 900 is similar in designs described above except that treatment region 914 includes a flexible protective cover 924. The cover serves to contain leaks of the cryogen in the event one of the fluid transport tubes is breached. Although a leak is not expected or anticipated in any of the fluid delivery transport tubes, the protective cover provides an extra or redundant barrier that the cryogen would have to penetrate in order to escape the catheter during a procedure. In embodiments the protective cover may be formed of metal.

Additionally, a thermally conducting liquid may be disposed within spaces or gaps between the transport tubes and the inner surface of the cover to enhance the device's thermal cooling efficiency during treatment. In embodiments the thermally conductive liquid is water.

Cover 924 is shown being tubular or cylindrically shaped and terminates at distal tip 912. As described herein, the cooling region 914 contains a plurality of fluid delivery and fluid return tubes to transport a cooling fluid through the treatment region 914 causing heat to be transferred/removed from the target tissue. In embodiments, the fluid is transported through the tube bundle under physical conditions near the fluid's critical point in the phase diagram for a first time period, and then the pressure is reduced for a second time period as described herein. The cover serves to, amongst other things, contain the cooling fluid and prevent it from escaping from the catheter in the event a leak forms in one of the delivery tubes.

Although a cover is shown in FIGS. 11-12, the invention is not intended to be so limited except as where recited in the claims. The apparatus may be provided with or without a protective cover and used to cool a target tissue.

Applications

The systems and methods described herein may be used in a wide variety of medical applications including, for example, oncology and cardiovascular applications. Candidate tumors to be ablated with cryoenergy include target tissues and tumors in the thorax, and upper and lower GI. The devices described herein may also be applied to destroy or reduce target tissues in the head and neck.

An exemplary cardiovascular application is endovascular-based cardiac ablation to create elongate continuous lesions. As described herein, creating elongate continuous lesions in certain locations of the heart can serve to treat various conditions such as, for example, atrial fibrillation. See, for example, Patent Application No. 61/981,110, filed Apr. 17, 2014, entitled Endovascular Near Critical Fluid Based Cryoablation Catheter Having Plurality of Preformed Treatment Shapes.

Methods and systems described herein serve to create lesions having a length ranging from 1-15 cm, or 2-10 cm., and more preferably between 5-8 cm. The lesions are preferably continuous and linear, not a series of spots such as in some prior art point-ablation techniques. In accordance with the designs described above, the cryoenergy and heat transfer may be focused on the endocardium, creating a lesion completely through the endocardium (a transmural lesion). Additionally, in embodiments, catheters achieve cooling power without vapor lock by modulating the pressure of the cooling fluid. The cooling fluid is preferably transported near its critical point in the phase diagram for at least a portion of the time of energy activation, and then optionally reduced to a lower pressure.

A cardiac ablation catheter in accordance with the principals of the present invention can be placed in direct contact along the internal lining of the left atrium, thereby avoiding most of the massive heat-sink of flowing blood inside the heart as the ablation proceeds outward.

Additionally, catheter configurations may include substantial bends, or loops which provide both the circumferential, as well as linear, ablations. The catheters described herein may be manipulated to form ring-shaped lesions near or around the pulmonary vessel entries, for example.

Many modifications and variations of the present invention are possible in light of the above teachings. It is therefore to be understood that within the scope of the appended claims the invention may be practiced otherwise than as specifically described.

I claim:

1. A cryoablation system comprising:
   a cryogen generator capable of providing a cryogenic fluid having a molar volume of gas and a molar volume of liquid;
   a cooler for cooling the cryogenic fluid;
   a medical device comprising a distal treatment section; and
   a controller operable to control cooling power delivered from the distal treatment section to create a lesion, wherein the controller modulates a pressure of the cryogenic fluid in the distal treatment section from a first fluid pressure to a second fluid pressure less than the first fluid pressure while the cryogenic fluid is transported through the distal treatment section, and wherein the first fluid pressure is at a near critical pressure of the cryogenic fluid such that the molar volume of gas and the molar volume of liquid are substantially equivalent, wherein the second fluid pressure is below the near critical pressure of the cryogenic fluid, and
   wherein modulating the pressure from the first fluid pressure to the second fluid pressure is carried out without increasing the molar volume of gas in the fluid, thereby avoiding vapor lock associated with cooling the medical device.

2. The cryoablation system of claim 1, wherein the medical device is a catheter.

3. The cryoablation system of claim 1, wherein the distal treatment section of the medical device comprises a temperature sensor.

4. The cryoablation system of claim 3, wherein the controller modulates the pressure based on a measured temperature from the temperature sensor.

5. The cryoablation system of claim 4, wherein the controller operates to change the first fluid pressure to the second fluid pressure when the measured temperature reaches −100° C. or less.

6. The cryoablation system of claim 4, wherein the controller is configured to determine whether the temperature at the temperature sensor is below a threshold value, wherein (i) if the temperature at the temperature sensor is not below the threshold value, the pressure is not reduced and (ii) if the temperature at the temperature sensor is below the threshold value, the pressure is reduced to a pre-set value.

7. The cryoablation system of claim 1, further comprising a high-pressure valve and a low-pressure valve, wherein the controller operates to switch the fluid path from the high-pressure valve to the low-pressure valve thereby decreasing the pressure of the fluid being transported through the distal treatment section of the medical device from the first fluid pressure to the second fluid pressure.

8. The cryoablation system of claim 1, further comprising a pressure regulator in fluid communication with the cryogen generator, and wherein the controller operates to control the pressure regulator to adjust the pressure from the first fluid pressure to the second fluid pressure.

9. The cryoablation system of claim 1, further comprising a piston in fluid communication with the cryogen generator, and wherein the controller operates to control the piston to adjust the pressure from the first fluid pressure to the second fluid pressure.

10. The cryoablation system of claim 1, further comprising a heat exchanger for reducing a temperature of the cryogenic fluid.

11. The cryoablation system of claim 1, wherein the cryogenic fluid is Nitrogen.

12. A method of treating target tissue, the method comprising:
    providing a medical device having a distal treatment section;
    positioning the distal treatment section of the medical device adjacent the target tissue;
    circulating a cryogenic fluid through the distal treatment section of the medical device for a first time period under physical conditions near a critical point of a liquid-vapor system for the cryogenic fluid,
    wherein the critical point defines a point in a phase diagram of the liquid-vapor system where molar volumes are substantially equivalent for liquid and gas, and whereby vapor lock associated with cooling of the medical device is avoided during the first time period; and
    decreasing a pressure of the cryogenic fluid in the distal treatment section of the medical device to a low pressure (PL) for a second time period subsequent to the first time period, wherein the low pressure (PL) is substantially less than a near critical pressure region of the cryogenic fluid, and whereby vapor lock associated with cooling of the medical device is avoided during the second time period.

13. The method of claim 12, wherein the cryogenic fluid is nitrogen.

14. The method of claim 12, wherein the first time period continues until a threshold temperature is reached.

15. The method of claim 12, wherein the physical conditions comprise pressure and the pressure is held substantially constant during the first time period.

16. The method of claim 12, wherein the physical conditions comprise a pressure and the pressure is varied during the first time period.

17. The method of claim 12, further comprising the step of determining whether the temperature at a temperature sensor in the medical device is below a threshold value, wherein (i) if the temperature at the temperature sensor is not below the threshold value, the pressure is not reduced and (ii) if the temperature at the temperature sensor is below the threshold value, the pressure is reduced to a pre-set value.

18. The method of claim 12, wherein the target tissue is cardiac tissue.

* * * * *